United States Patent
Mayr

(10) Patent No.: US 12,272,226 B2
(45) Date of Patent: Apr. 8, 2025

(54) PROTECTION SYSTEM FOR A POWER TOOL

(71) Applicant: EINHELL GERMANY AG, Landau/Isar (DE)

(72) Inventor: Stefan Mayr, Landau/Isar (DE)

(73) Assignee: EINHELL GERMANY AG, Landau/Isar (DE)

( * ) Notice: Subject to any disclaimer, the term of this patent is extended or adjusted under 35 U.S.C. 154(b) by 57 days.

(21) Appl. No.: 18/315,268

(22) Filed: May 10, 2023

(65) Prior Publication Data

US 2023/0368638 A1 Nov. 16, 2023

(30) Foreign Application Priority Data

May 13, 2022 (DE) ...................... 20 2022 102 628.9

(51) Int. Cl.
  *G08B 21/18* (2006.01)
  *B25F 5/00* (2006.01)
  *G08B 3/00* (2006.01)

(52) U.S. Cl.
  CPC .............. *G08B 21/187* (2013.01); *B25F 5/00* (2013.01); *G08B 3/00* (2013.01)

(58) Field of Classification Search
  CPC ................................ G08B 21/187; B25F 5/00
  See application file for complete search history.

(56) References Cited

U.S. PATENT DOCUMENTS

| | | | | |
|---|---|---|---|---|
| 2014/0151079 A1* | 6/2014 | Furui | ..................... | H02J 7/0042 173/171 |
| 2019/0083320 A1 | 3/2019 | Gustavsson et al. | | |

FOREIGN PATENT DOCUMENTS

| | | | | | |
|---|---|---|---|---|---|
| EP | 3610989 | A1 | | 2/2020 | |
| EP | 3445065 | B1 | | 10/2020 | |
| EP | 3902296 | A1 | | 10/2021 | |
| RU | 2016119860 | | * | 5/2016 | |
| SE | 543197 | | * | 7/2019 | ............. B27G 21/00 |
| WO | WO 2006107464 | | * | 2/2006 | ........... H04R 29/008 |
| WO | 2016203315 | A3 | | 12/2016 | |

OTHER PUBLICATIONS

European Search Report issued Oct. 5, 2023 in EP Appl. No. 23 172 709.0.

* cited by examiner

*Primary Examiner* — Hongmin Fan
(74) *Attorney, Agent, or Firm* — MEDLER FERRO WOODHOUSE & MILLS PLLC

(57) ABSTRACT

A protection system for a power tool is disclosed having a battery pack. The batter pack may be used with the power tool to supply an electrical consumer of the power tool with electrical energy, as well as hearing protection for a user of the power tool. The battery pack has a first control circuit, which is set up to, directly or indirectly, provide information relating to a value of an operating parameter of the power tool to a second control circuit of a hearing protector. The hearing protector has an audio output device, and the second control circuit is set up for this purpose, the audio output device uses the transmitted information to control generation of an audible warning output.

20 Claims, 1 Drawing Sheet

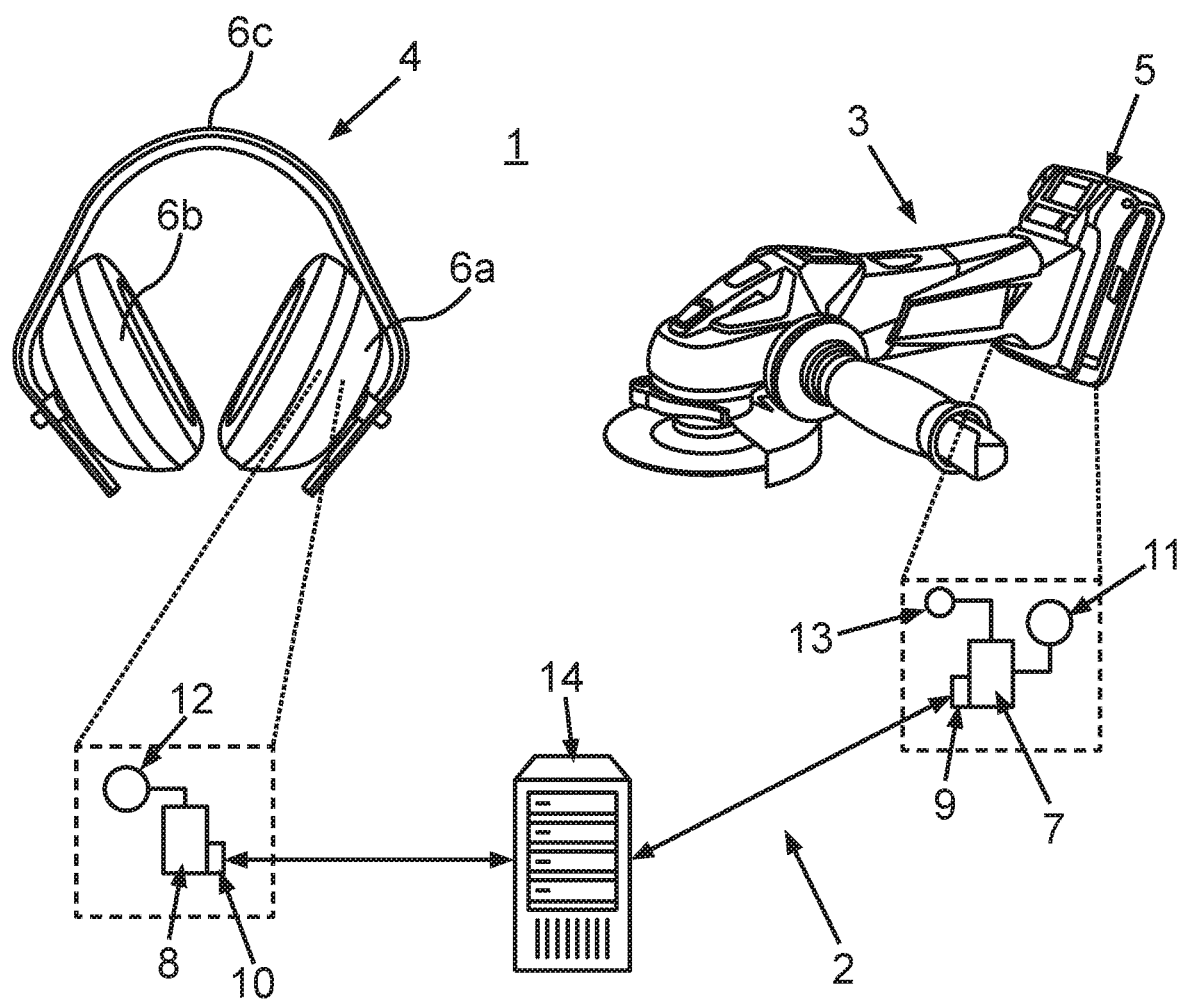

PROTECTION SYSTEM FOR A POWER TOOL

FIELD

The present invention relates to a protection system for a power tool and a power tool system comprising such a protection system.

BACKGROUND

In the case of power tools, in particular power tools for cutting, grinding or drilling, there may be involved a heavy load or overload of the electrical load on the electrical load of the power tool, in particular of an electric motor of the power tool, and/or a heavy load or overload of the electronic system, if the electrical load is counteracted by a very high resistance through the workpiece to be processed. In the case of battery-operated power tools, such overload may also lead to a damage of accumulator cells. This may in particular be relevant if a user themselves provides for a feed of the power tool with regard to the workpiece or at least in part such manual feed is provided, as is the case for instance in circular hand saws, angle grinders, drills or other power tools for cutting, grinding or drilling. Moreover, it may be possible, in particular if the electric appliance is operable with a battery pack, for instance an exchangeable battery pack, that a maximum current output of the battery pack is higher than a maximum current admissible or tolerable for the electrical load so that the electrical load possibly might be damaged.

It is known to monitor the current consumption and/or temperature of the electrical load of a power tool and to possibly switch off the power tool if the current consumption and/or temperature exceeds a respective admissible limiting value. However, on the one hand, this is disadvantageous in terms of user comfort, since the user is interrupted in his or her work. Moreover, the interruption of the operation of the power tool possibly leads to a loss in quality when processing the workpiece, in particular when blades are brought to a standstill. Besides, in such an approach the admissible limiting value for the current must be designed relatively conservatively. A disadvantage of the temperature-dependent shutdown may be that it may take relatively long for the electrical load to have sufficiently cooled down.

SUMMARY

It is an objective of the present invention to provide a possibility for protection of a power tool or its components against overload, by which a forced shutdown of the power tool is avoided if possible.

This objective is solved by the subject matter of the independent claim. Advantageous further developments and preferred embodiments are subject matter of the dependent claims.

The invention is based on the idea to couple a battery pack for the power tool in such a way with a hearing protection for a user of the power tool that the battery pack causes the hearing protection to generate via an audio output device an acoustic warning message depending on a value of an operating parameter of the power tool.

According to an aspect of the invention a protection system for a power tool is indicated, the protection system comprising a battery pack, which is connectable with the power tool for supplying an electrical load, in particular of an electric motor, of the power tool with electric current. The protection system comprises a hearing protection for a user of the power tool that is in particular provided separate from the power tool and the battery pack. The battery pack comprises a first control circuit, the hearing protection comprises a second control circuit. The first control circuit is configured for transmitting an information concerning a value of an operating parameter of the power tool directly or indirectly to the second control circuit of the hearing protection. The hearing protection comprises an audio output device, for example one or more loudspeakers, and the second control circuit is configured to control the audio output device depending on the transmitted information to generate an acoustic warning output.

The operating parameter may for instance correspond to an operating current of the electrical load, for instance a current output by an energy source, in particular a battery pack, during the operation of the power tool to the electrical load, in particular the electric motor. Depending on the implementation of the power tool and the electrical load, however, also other operating parameters may be used, such as an operating voltage, for instance an output voltage of the battery pack, a charging state of the battery pack, a temperature, for instance a temperature of an electronic component of the power tool or the electrical load, a fluidic flow of an operating medium, that is in particular a fluidic flow rate or a fluidic flow velocity, or a combination of the named quantities, such as a product of fluidic pressure and fluidic flow velocity, an electric power or the like. The operating parameter may also be a derived quantity, such as a torque, which may for example be derived from signatures occurring in the operating current or the output voltage, so-called ripples.

The communication between the battery pack, in particular the first control circuit, and the hearing protection, in particular the second control circuit, may in principle be conducted wirelessly or wire-based. Preferably the communication is conducted wirelessly, for instance via radio communication. In particular the protection device may comprise a first communication interface for the battery pack connected to the first control circuit and a second communication interface for the hearing protection connected to the second control circuit.

The transmission of the information may then be effected directly or indirectly from the first communication interface to the second communication interface. Direct transmission in this connection may be understood to mean that by the first communication interface a radio signal or a wire-based signal is generated and is directly, without interposition of a further unit, transmitted to the second communication interface and thus to the second control circuit. An indirect communication or an indirect transmission or transfer of the information may be understood to mean that by the communication interface the signal, to start with, is transmitted to the further unit, for instance an external computing unit, and is then transmitted by the same to the second communication interface and thus the second control circuit.

In particular the signals used in the transmission of the information may also be processed or changed for the transmission of the information, however, therein the information remains maintained.

The wireless transmission of the information from the first control circuit or the first communication interface, respectively, to the second control circuit or the second communication interface of the, respectively, may for instance be realized according to a GSM standard, a standard based on the GSM standard, Edge, UMTS, HSDPA, LTE, or another mobile radio standard. The transmission may for instance also be based on LTE-M, LTE-CAT-M1 or another standard. The transmission may also be effected according to a "Narrow Band Internet of Things", NB-IOT, or another "Low Power White Area Network", LPWAN. The transmission may also be effected according to any other radio standard, such as according to Bluetooth or WLAN.

The battery pack, alone or in some embodiments together with one or more further battery packs, is designed and configured to supply the electrical load, in particular the electric motor, of the power tool with energy. The first control circuit may for instance be part of a battery management system of the battery pack.

The battery pack may releasably, in particular non-destructively releasably, be connected to a housing of the power tool, for example via a snap-fit connection, a plug-in connection and/or a clamping connection. In particular the mechanical connection of the battery pack to the housing of the power tool may be designed as form-fit and/or force-fit connection without a substance bonding being given. In other words, the mechanical connection of the battery pack to the housing of the power tool may be released without having to release a substance bonding. Preferably, the mechanical connection may, according to its intended purpose, be released manually without employing other tools. In other words, the battery pack is designed as exchange battery pack, in particular system battery pack. For electrical and mechanical connection the housings of the battery pack and of the power tool may comprise respective interfaces.

An electrical connection of the at least one accumulator cell with the power tool, in particular the electrical load, may for instance be effected via one or more releasable electric contacts, for instance clamping contacts or plug-in contacts, in particular so-called tulip contacts or blade contacts. For example at the interfaces of the corresponding housings mutually compatible plugs or sockets, or receptacles, respectively, or the like may be provided in each case to achieve the electrical connection of the battery pack with the power tool.

By the protection system according to the invention on the basis of the acoustic warning output the user of the power tool, who for example wears the hearing protection, may immediately be informed or warned, respectively, about the value of the operating parameter, for instance in relation to one or more limiting values.

The invention in this connection advantageously makes use of a specific acoustic information channel via the hearing protection, in particular in an interior of an ear cup of the hearing protection. If the user wears the hearing protection, he or she may therefore perceive the acoustic warning output, since inherent noise of the power tool or noise caused by the interaction with the workpiece is blocked or at least reduced by the hearing protection.

Advantageously the acoustic warning message may be generated dynamically, for instance by a change of the warning tone, a pitch of the warning tone, a frequency of acoustic pulses of the warning signal and so on, in particular depending on the value of the operating parameter. In this way by a simple acoustic communication channel a relatively high information density may be provided to the user, which is easy for him or her to capture and to respond to, if need be.

In this connection it is particularly advantageous to generate the warning output by the hearing protection, for example in the interior of the, since the warning output due to environmental noise reduced by the hearing protection may be perceived particularly well and reliably.

By the acoustic warning output, ideally a shutdown of the power tool may be done without if the value of the operating parameter approaches a critical value, since the situation and the value of the operating parameter may, accordingly, be pointed out early and preferably dynamically. In other words, the invention realizes a proactive strategy for avoiding critical states in contrast to a responsive strategy, for instance by consequently shutting down the current supply or limiting the current supply. In comparison with a temperature-dependent shutdown a forced cooling pause of the electrical load can be avoided.

In addition to the control of the lighting device depending on the transmitted information according to the invention, in some embodiments still a current-dependent and/or temperature-dependent shutdown of the electrical load may be provided, for instance if the user does not or not sufficiently respond to the control of the lighting device.

Thus, not only the user comfort when using the power tool may be improved, but also a loss in quality in the work results can be avoided, since the tool, if possible, is not stopped in-between operation and needs to start running again, which may lead to suboptimal transitions on the surface of the workpiece and so on, depending on the kind of power tool.

Moreover, also the electrical load is reliably protected, since reaching the critical state may be avoided, if possible. In particular an overload of the electric motor by excessive resistance due to excessive feed by the user can be avoided as well as an overload of the accumulator cells in the case of a battery-operated power tool and/or the electronics of the battery pack or of the power tool.

The power tool, which may also be a gardening tool, is for example a power tool for sawing, for cutting or for drilling. This means it may for example be a saw, for example a jigsaw, a chop saw, a table circular saw, a hand-held circular saw, a chain saw, a high pruner, a band saw and so on. It may also be a milling machine, an angle grinder, a stone cutter, a tile cutter, a planer, a thickness planer, a turning lathe, and so on. Moreover, it may be a drilling machine, a percussion drill, a rotary hammer drill, and so on. This list is to be understood as merely exemplary and non-exhaustive and does not limit the applicability of the invention in principle.

In particular in the case of power tools for cutting, grinding or drilling, however, commonly an at least in part manual feed is to be performed by a user. In other words, the user possibly has immediate influence upon the load of the power tool, in particular an electrical load, for example an electric motor, by influencing the feed. In extreme cases, by acting correspondingly upon the power tool, the user may for example even provoke a standstill of the electric motor. In particular in the case of such power tools the invention may therefore be advantageously employed.

According to at least one embodiment of the protection system the first control circuit is configured to transmit the information via the first communication interface and the second communication interface directly to the second control circuit.

In alternative embodiments the protection system comprises an external computing unit and the first control circuit is configured to transmit the information via the first communication interface to the first computing unit and the external computing unit is configured to transmit the information via the second communication interface to the second control circuit, in particular to transmit the information indirectly from the first control circuit to the second control circuit.

The external computing unit is neither part of the power tool nor of the battery pack nor of the hearing protection, this means it is arranged external both to the power tool as well as to the battery pack and to the hearing protection. The external computing unit may for example be a server computer system or a cloud computer system or the like.

According to at least one embodiment, the hearing protection is designed as capsule ear protection and comprises an, in particular auricle-surrounding, wherein the audio output device is for example arranged in the ear cup.

Thereby the acoustic warning output may be output directly on the ear of the user so that he or she may perceive it particularly well.

The hearing protection comprises in particular a further ear cup connected by a headband to the ear cup. The second control circuit may be arranged in the ear cup or the further ear cup or in or, as the case may be, on the headband.

According to at least one embodiment the battery pack comprises a sensor that is arranged and configured to generate a sensor signal depending on the value of the operating parameter.

According to at least one embodiment the first control circuit is configured to receive a sensor signal from the electrical appliance depending on the value of the operating parameter, in particular from a sensor of the electrical appliance.

According to at least one embodiment, the sensor signal corresponds to an operating current for operating an electrical load of the power tool or a current output by at least one accumulator cell of the battery pack to the electrical appliance. This means that the sensor of the battery pack or of the electrical appliance is in particular designed as current sensor.

The operating current or the output current represent a particularly reliable and easy to determine characteristic for the load of the electrical load and/or the battery pack, in particular the accumulator cells.

According to at least one embodiment, the information concerning the value of the operating parameter contains the value of the operating parameter. The second control circuit is configured to control the audio output device depending on the value of the operating parameter to generate the acoustic warning output.

According to at least one embodiment, the second control circuit is configured to compare the value of the operating parameter with at least one predetermined limiting value and to control the audio output device depending on a result of the comparison to generate the acoustic warning output.

According to at least one embodiment, the first control circuit is configured to compare the value of the operating parameter with at least one predetermined limiting value and the information concerning the value of the operating parameter contains a result of the comparison. The second control circuit is configured to control the audio output device depending on the result of the comparison to generate the acoustic warning output.

For example a first limiting value of the at least one limiting value may define an admissible operating range. For example the admissible operating range may correspond to a value of the operating parameter smaller or equal to the first limiting value.

In this case a volume and/or repetition rate and/or pitch of the acoustic warning message may for example be the higher the smaller the distance of the value of the operating parameter from the first limiting value. The respective variation of the acoustic warning message may in this connection be effected continuously or in discrete steps, in particular in two or more discrete steps.

Also a second limiting value may be provided, which defines an inadmissible operating range. If the value of the operating parameter for instance is equal to or larger than the second limiting value, the inadmissible operating range may be given. In this case the volume and/or repetition rate and/or pitch of the acoustic warning message may for example also be determined depending on a difference between the second limiting value and the value of the operating parameter, if the value of the operating parameter is larger than the second limiting value. For example the volume and/or repetition rate and/or pitch of the acoustic warning message may be the higher the more the value of the operating parameter deviates from the second limiting value.

According to at least one embodiment the hearing protection, for instance the second control circuit, comprises a memory unit, which stores at least one output information. The second control circuit is configured to generate the audio output device depending on the at least one output information to generate the acoustic warning message.

The at least one output information contains at least two or more different pieces of output information. The second control circuit is configured to select one of the two or more different pieces of output information depending on the transmitted information. The second control circuit is configured to control the audio output device to generate the acoustic warning output according to the selected output information.

In this way through different pieces of output information it may be dynamically responded to the value of the operating parameter.

According to a further aspect of the invention a power tool system comprising a power tool and protection system for the power tool according to the invention is indicated.

According to at least one embodiment of the power tool system the power tool is designed as power tool for cutting, grinding or drilling and/or as gardening tool.

According to at least one embodiment, the power tool is designed such that during operation of the power tool an at least in part manual feed by a user is provided.

The first control circuit may for example be designed as first computing unit or be comprised by a first computing unit. The second control circuit may for example be designed as a second computing unit or be comprised by a second computing unit.

A computing unit may in particular be understood as a data processing device, which contains a processing circuit. This means that the computing unit may process in particular data for performing computing operations. These possibly also include operations to perform indexed accesses to a data structure, for example a look-up table, LUT.

In particular, the computing unit may include one or more computers, one or more microcontrollers, and/or one or more integrated circuits, for example, one or more application-specific integrated circuits, ASIC, one or more field-programmable gate arrays, FPGA, and/or one or more systems on a chip, SoC. The computing unit may also include one or more processors, for example one or more microprocessors, one or more central processing units, CPU, one or more graphics processing units, GPU, and/or one or more signal processors, in particular one or more digital signal processors, DSP. The computing unit may also include a physical or a virtual cluster of computers or other of the said units.

In various embodiments the computing unit comprises one or more hardware and/or software interfaces and/or one or more memory units.

A memory unit may be implemented as a volatile data memory, for example a dynamic random access memory, DRAM, or a static random access memory, SRAM, or as a non-volatile data memory, for example a read-only memory, ROM, a programmable read-only memory, PROM, an erasable programmable read-only memory, EPROM, an electrically erasable programmable read-only memory, EEPROM, a flash memory or flash EEPROM, a ferroelectric random access memory, FRAM, a magnetoresistive random access memory, MRAM, or a phase-change random access memory, PCRAM.

If within the scope of the present disclosure it is mentioned that a component of the protection system according to the invention or of the power tool according to the invention, in particular the first control circuit, the second or first control circuit, the external computing unit or any other computing unit of the protection system or the power tool is configured, designed, construed, or the like to perform or realize a certain function, to achieve a certain effect, or to serve a certain purpose, this may be understood such that the component, beyond the principal or theoretical employability or applicability of the component for this function, effect or this purpose, through a corresponding adaptation, programming, physical design, and so on, concretely and actually is capable of performing or realizing the function, to achieve the effect, or to serve the purpose.

Further features of the invention derive from the claims, the figures, and the description of the figures. The features and feature combinations mentioned before in the description as well as named in the following in the description of the figures and/or shown in the figures may be comprised by the invention not only in the respective indicated combination, but also in other combinations. In particular also embodiments and feature combinations may be comprised by the invention that do not comprise all features of an originally formulated claim. Moreover, embodiments and feature combinations may be comprised by the invention which go beyond the feature combinations set out in the back-references of the claims or deviate therefrom.

BRIEF DESCRIPTION OF FIGURES

The invention is explained in more detail in the following by reference to the concrete embodiments and associated schematic drawings.

FIG. 1 depicts a schematic representation of an exemplary embodiment of a power tool system according to the invention.

DETAILED DESCRIPTION

In FIG. 1 an exemplary embodiment of a power tool system 1 according to an embodiment of the invention is shown, which comprises a power tool 3, merely exemplarily represented as angle grinder, and an exemplary embodiment of a protection system 2 for the power tool 3 according to the embodiment.

The protection system 2 comprises a battery pack 5 comprising accumulator cells 11, which is connectable to the power tool 3 for supplying an electrical load, in particular an electric motor (not shown) of the power tool 3 with electric energy, as well as a hearing protection 4, exemplarily represented as capsule ear protection with two ear cups 6a, 6b and a headband 6c connecting the ear cups 6a, 6b.

The protection system 2 comprises a sensor 13 of the power tool 3 or the battery pack, which is arranged and configured to determine or to measure a value of the operating parameter of the power tool 3 and to generate a sensor signal depending on the value of the operating parameter of the power tool 3.

The sensor 13 may for instance be designed as current sensor and the operating parameter may correspond to a current from the battery pack 5 or the accumulator cells 11 to the electric motor. Depending on the power tool 3 other operating parameters and corresponding sensors 13 are also possible.

The battery pack 5 comprises a control circuit 7, which is configured to transmit depending on the sensor signal an information concerning the value of the operating parameter to a second control circuit 8 of the hearing protection 4.

The hearing protection 4 comprises an audio output device 12, for example a loudspeaker, and the second control circuit 8 is configured to control the audio output device 12 depending on the transmitted information to generate an acoustic warning output.

The second control circuit 8 and/or the audio output device 12 may for example be arranged in one of the ear cups 6a, 6b so that the audio output device 12 may output the acoustic warning output in the direction of an ear of the user when the same is wearing the hearing protection according to the intended purpose.

The first control circuit 7 is configured to transmit an information concerning the value of the operating parameter depending on the sensor signal directly to the second control circuit 8, in particular via a first communication interface 9 of the battery pack 5, for example the first control circuit 7, and a second communication interface 10 of the hearing protection 4. Alternatively the first control circuit 7 may transmit the information concerning the value of the operating parameter depending on the sensor signal via the first communication interface 9 to the external computing unit 14, in particular a cloud server or the like, of the protection system 2, and the external computing unit 14 may transmit the information concerning the value of the operating parameter to the second communication interface 10 and thus to the second control circuit 8.

LIST OF REFERENCE SIGNS 1 power tool system
2 protection system
3 power tool
4 hearing protection
5 battery pack
6a, 6b ear cups
6c headband
7, 8 control circuits
9, 10 communication interfaces
11 accumulator cells
12 audio output device
13 sensor
14 external computing unit

What is claimed is:

1. A protection system for a power tool, the protection system comprising:
a battery pack, which is connectable with the power tool for supplying an electrical load of the power tool with electric energy, as well as a hearing protection for a user of the power tool,
wherein the battery pack comprises a first control circuit, which is configured to transmit an information concerning a value of an operating parameter of the power tool directly or indirectly to a second control circuit of the hearing protection; and wherein the hearing protection comprises an audio output device and the second control circuit is configured to control the audio output device depending on the transmitted information to generate an acoustic warning output.

2. The protection system according to claim 1, wherein the hearing protection is designed as a capsule ear protection and comprises an ear cup.

3. The protection system according to claim 2, wherein the audio output device is arranged in the ear cup.

4. The protection system according to claim 1, wherein the first control circuit is configured to receive a sensor signal depending on the value of the operating parameter from the power tool.

5. The protection system according to claim 1, wherein the battery pack comprises a sensor, which is configured to generate a sensor signal depending on the value of the operating parameter.

6. The protection system according to claim 5, wherein the sensor signal corresponds to an operating current for operating an electrical load of the power tool or to a current output by one of at least one accumulator cell of the battery pack to the power tool.

7. The protection system according to claim 4, wherein the first control circuit is configured to transmit the information concerning the value of the operating parameter depending on the sensor signal to the second control circuit.

8. The protection system according to claim 1, wherein the battery pack comprises a first communication interface connected to the first control circuit; and wherein the hearing protection comprises a second communication interface connected to the second control circuit.

9. The protection system according to claim 8, wherein the first control circuit is configured to transmit the information via the communication interface and the second communication interface directly to the second control circuit.

10. The protection system according to claim 8, wherein the protection system comprises an external computing unit;

the first control circuit is configured to transmit the information via the first communication interface to the external computing unit; and the external computing unit is configured to transmit the information via the second communication interface to the second control circuit.

11. The protection system according to claim 1, wherein the information concerning the value of the operating parameter comprises the value of the operating parameter; and wherein the second control circuit is configured to control the audio output device depending on the value of the operating parameter to generate the acoustic warning output.

12. The protection system according to claim 11, wherein the second control circuit is configured to compare the value of the operating parameter with at least one predetermined limiting value and to control the audio output device depending on a result of the comparison to generate the acoustic warning output.

13. The protection system according to claim 12, wherein the first control circuit is configured to compare the value of the operating parameter with the at least one predetermined limiting value and the information concerning the value of the operating parameter comprises a result of the comparison; and wherein the second control circuit is configured to control the audio output device depending on the result of the comparison to generate the acoustic warning output.

14. The protection system according to claim 1, wherein the hearing protection comprises a memory unit, which stores at least one output information; and wherein the second control circuit is configured to control the audio output device depending on the at least one output information to generate the acoustic warning output.

15. A protection system for a power tool, the protection system comprising:

a battery pack, which is connectable with the power tool for supplying an electrical load of the power tool with electric energy, as well as a hearing protection for a user of the power tool, wherein the battery pack comprises a first control circuit, which is configured to transmit an information concerning a value of an operating parameter of the power tool directly or indirectly to a second control circuit of the hearing protection; and wherein the hearing protection comprises an audio output device and the second control circuit is configured to control the audio output device depending on the transmitted information to generate an acoustic warning output, wherein the hearing protection comprises a memory unit, which stores at least one output information; and wherein the second control circuit is configured to control the audio output device depending on the at least one output information to generate the acoustic warning output, wherein the at least one output information comprises two or more different pieces of output information;

the second control circuit is configured to select one of the two or more different pieces of output information depending on the transmitted information; and the second control circuit is configured to control the audio output device to generate the acoustic warning output according to the selected output information.

16. A power tool system comprising:

a power tool; and a protection system for the power tool according to claim 1.

17. The power tool system according to claim 16, wherein the power tool is designed as a power tool for cutting, grinding or drilling, or as a gardening tool.

18. The power tool system according to claim 16, wherein the power tool is designed such that during operation of the power tool an at least in part manual feed by the user is provided.

19. The protection system according to claim 1, wherein the acoustic warning is generated dynamically depending on the value of the operating parameter.

20. The protection system according to claim 1, wherein a change in a volume, repetition rate, pitch, or frequency of the acoustic warning is generated dynamically depending on the value of the operating parameter.

* * * * *